United States Patent
Granz et al.

(10) Patent No.: US 7,281,429 B2
(45) Date of Patent: Oct. 16, 2007

(54) OPTICAL HYDROPHONE FOR A SHOCK-WAVE FIELD WITH LONG SERVICE LIFE

(75) Inventors: Bernd Granz, Oberasbach (DE); Ralf Nanke, Spardorf (DE)

(73) Assignee: Siemens Aktiengesellschaft, Munich (DE)

( * ) Notice: Subject to any disclaimer, the term of this patent is extended or adjusted under 35 U.S.C. 154(b) by 138 days.

(21) Appl. No.: 10/535,804

(22) PCT Filed: Oct. 7, 2003

(86) PCT No.: PCT/DE03/03320

§ 371 (c)(1),
(2), (4) Date: May 23, 2005

(87) PCT Pub. No.: WO2004/051203

PCT Pub. Date: Jun. 17, 2004

(65) Prior Publication Data

US 2006/0012775 A1    Jan. 19, 2006

(30) Foreign Application Priority Data

Nov. 29, 2002 (DE) ................................ 102 56 077
Aug. 1, 2003 (DE) ................................ 103 35 988

(51) Int. Cl.
*G01D 5/32* (2006.01)
(52) U.S. Cl. ...................... 73/655; 73/299; 250/227.25; 367/149
(58) Field of Classification Search ................ 73/655, 73/653, 657, 861.42, 299; 356/128, 349, 356/351, 342, 233; 367/649, 657, 141, 149, 367/167; 250/227.25, 227.21
See application file for complete search history.

(56) References Cited

U.S. PATENT DOCUMENTS

| 3,611,277 A | 10/1971 | Yoder |
| 4,471,474 A * | 9/1984 | Fields ........................ 367/149 |
| 5,010,248 A | 4/1991 | Eisenmenger et al. . 250/227.21 |
| 5,017,775 A * | 5/1991 | Granz et al. ........... 250/227.25 |

(Continued)

FOREIGN PATENT DOCUMENTS

DE         38 02 024 A1    8/1989

(Continued)

OTHER PUBLICATIONS

"Fibre-Optic Probe Hydrophone for Ultrasonic and Shock-wave Measurements in Water," Staudenraus et al., Ultrasonics, vol. 31, No. 4 (1993) pp. 267-273.

(Continued)

*Primary Examiner*—Hezron Williams
*Assistant Examiner*—Jacques M. Saint-Surin
(74) *Attorney, Agent, or Firm*—Schiff Hardin LLP

(57) ABSTRACT

An optical hydrophone for measurement of the acoustic pressure distribution in a fluid medium has a light source that illuminates an area of a boundary region between an optically transparent body and the fluid medium. A light receiver measures the intensity of the light reflected from the illuminated area as a measurement of acoustic pressure, due to changes in the index of refraction of the fluid medium that are caused by the acoustic pressure. The illuminated area is smaller than the boundary surface formed between the optically transparent body and the fluid medium, thereby giving the hydrophone a longer service light and a high spatial resolution capacity.

13 Claims, 2 Drawing Sheets

U.S. PATENT DOCUMENTS

| | | | |
|---|---|---|---|
| 5,315,364 A | | 5/1994 | Arion et al. |
| 5,353,262 A | * | 10/1994 | Yakymyshyn et al. ...... 367/149 |
| 5,488,853 A | | 2/1996 | Niewisch et al. |
| 5,636,181 A | * | 6/1997 | Duggal ........................ 367/149 |
| 5,732,046 A | * | 3/1998 | O'Donnell et al. ......... 367/149 |
| 6,172,376 B1 | * | 1/2001 | Xu et al. ..................... 250/574 |
| 6,517,512 B1 | * | 2/2003 | Bock et al. .................... 604/67 |
| 6,538,739 B1 | * | 3/2003 | Visuri et al. ................ 356/394 |
| 6,594,290 B2 | * | 7/2003 | Toida ............................ 372/28 |
| 7,057,973 B2 | * | 6/2006 | Ferrell ......................... 367/131 |
| 2006/0241495 A1 | * | 10/2006 | Kurtz .......................... 600/476 |

FOREIGN PATENT DOCUMENTS

| | | |
|---|---|---|
| DE | 39 32 711 A1 | 4/1991 |
| DE | 195 41 952 A1 | 5/1997 |
| DE | 197 41 747 C1 | 8/1998 |
| DE | 197 08 806 C1 | 9/1998 |
| WO | WO89/06512 | 7/1989 |

OTHER PUBLICATIONS

"Coated Fiber-Optic Hydrophone for Ultrasonic Measurement," Koch, Ultrasonics, vol. 34, (1996) pp. 687-689.

An Optical Detection System for Biomedical Photoacoustic Imaging, Beard et al., Proc. SPIE 3916 (2000) pp. 100-109.

Photoacoustic Imaging of Blood Vessel Equivalent Phantoms, Beard, Proc. SPIE 4618 (2002), pp. 54-62.

"Measurement of Laser-Induced Acoustic Waves with a Calibrated Optical Transducer," Paltauf et al., J. Appl. Phys., vol. 82, No. 4, Aug. 15, 1997, pp. 1525-1531.

"Novel Technique of Interferometric Optical Fiber Sensing," Shelyakov et al., SPIE, vol. 2349 (1995), pp. 154-157.

* cited by examiner

OPTICAL HYDROPHONE FOR A SHOCK-WAVE FIELD WITH LONG SERVICE LIFE

BACKGROUND OF THE INVENTION

1. Field of the Invention

The invention concerns an optical hydrophone for measurement of the acoustic pressure distribution in a fluid medium, in particular for measurement of an ultrasonic shockwave field or of diagnostic ultrasound.

2. Description of the Prior Art

With acoustic shockwaves as they are used, for example, in lithotripsy, high pressures (up to approximately $10^8$ Pa) occur with rise times of a few ns. The measurement of such high pressures requires sensors with a high mechanical stability. Moreover, these sensors should be miniaturized to a large extent in order to be able to measure the acoustic pressure distribution in a shockwave field with optimally high spatial resolution.

Measurement arrangements in which the light reflected at the free end of a fiber optic cable is used for measurement of the spatial and temporal distribution of the pressure of ultrasound shockwaves in a fluid are respectively known from EP 0 354 229 B1 and DE 38 02 024 A1 as well as from J. Staudenraus, W. Eisenmenger, "Fibre-optic probe hydrophone for ultrasonic and shock-wave measurements in water", Ultrasonics 1993, Vol. 31, No. 4, page 267-273. This known fiber-optic measurement arrangement makes use of the fact that the high pressure amplitude generates a density change (and thus a change of the index of refraction of the fluid) in the immediate proximity of the free end that modulates the fraction of the light reflected back into the fiber optic cable at the boundary surface. The fiber optic cables used for measurement thereby have a diameter that does not exceed 0.1 mm. The free end of the fiber optic cable that determines the reflectivity of the fluid/fiber optic cable boundary is formed by a spherical or planar end surface standing perpendicular to the fiber optic cable axis. A high spatial resolution, the low directional sensitivity and the high bandwidth that are necessary for the measurement of focused shockwaves are achieved by the minuteness of this end surface.

A fiber-optic shockwave sensor in which the free end of the fiber optic cable is designed as a rotation body whose envelope can be described by a polynomial of the third degree is known from DE 39 32 711 A1. Both the sensitivity and the spatial resolution should be improved via these measures, also given the use of fiber optic cables with a larger diameter.

A fiber-optic hydrophone that uses both changes of the index of refraction of the surrounding fluid and the change of the properties of an interferometer formed at the fiber tip by dielectric layers, in order to increase the sensitivity of the measurement arrangement in this manner, is known from Koch, Ch., "Coated fiber-optic hydrophone for ultrasonic measurement", Ultrasonics 34, 1996, page 687-689.

A disadvantage of the known fiber-optic hydrophones is that they are very sensitive to breakage and can already be destroyed after 10 to 100 shockwaves at approximately 50 MPa. Moreover, a high production-related expenditure is necessary in order to reproducibly manufacture the free ends of the fiber optic cables with the necessary shape.

Interferometric measurement arrangements in which a polymer film serves as a large-area Fabry-Perot interferometer, that is optically sampled point-by-point such that a two-dimensional image of the acoustic pressure distribution results, are also know in the literature, for example in Beard, P C, Mills T N, "An optical detection system for biomedical photoacoustic imaging", Proc. SpiE 3916, 2000, page 100-109, or Beard, P C, "Photoacoustic imaging of blood ressel equivalent phantoms", Proc. SpiE 4618, 2002, page 54-62. Such an apparatus, however, is not suitable for the measurement of shockwaves.

SUMMARY OF THE INVENTION

An object of the present invention is to provide an optical hydrophone for measurement of the acoustic pressure distribution in a fluid medium that can be produced simply, exhibits a high lifespan and whose spatial resolution capability is comparable with the spatial resolution capability that can be achieved by the fiber-optic hydrophone known in the prior art.

The above object is achieved according to the invention by an optical hydrophone having a light source for generation of light and for illumination of an area located at a boundary surface between an optically-transparent body and the sound-conducting medium, as well as a measurement device for measurement of the intensity of a light reflected at this area as a measure for the sound pressure, wherein the illuminated area is smaller than the boundary surface formed between the body and the medium.

The invention is based on the recognition that achieving a high spatial resolution depends only on the size of the area illuminated at the boundary surface between the transparent body and the sound-conducting medium. In other words: the transparent body does not necessarily have to be designed as a light conductor in which the light is conducted via reflection at the walls. Rather, it is sufficient to generate, by a suitable beam formation, a light beam that freely propagates in the transparent body that exhibits a beam cross-section adapted (by the beam formation) to the required purpose in the region of the boundary surface. In this manner, the transparent body can exhibit dimensions that are significantly larger than the beam cross-section and can be executed relatively large, such that it cannot be destroyed by shockwaves as occur in the focus of a lithotripter. Moreover, the boundary surface can be processed without problems, such that a high reproducibility with a low production-related expenditure can be achieved.

A measurement arrangement for measurement of the absorption of a short laser pulse in a probe, in which the shockwaves generated in the probe by the laser beam are emitted into a chamber filled with water and there lead to a modulation of the index of refraction is known from G. Paltauf et al., "Measurement of laser-induced acoustic waves with a calibrated optical transducer", J. Appl. Phys. 82 (4), 1997, p. 1525-1531. The chamber borders the base surface of a glass prism into which light is laterally injected and there propagates freely, i.e. without reflection on boundary surfaces, and impinges on the base surface under at the critical angle of total reflection. The modulation (caused by the modulation of the index of refraction) of the fraction of the light reflected on the base surface is measured and used as a measure for the laser power absorbed in the probe. Although the same physical effects are used in this arrangement as in the known fiber-optic hydrophones, these cannot be used at such an indirect measurement of the absorbed laser power since they would influence the propagation of the laser beam. For this reason, the light is laterally injected into a prism frustrum whose base surface is perpendicular to the propagation direction of the laser beam and that is transparent for this laser beam, such that the light can pass unhindered through the prism frustrum. Moreover, the measurement of the distribution of the sound field does not dominate the measurement arrangement since it depends only on the entire laser power absorbed within the probe.

The invention is based on the realization that the basic concept used in this known measurement arrangement (namely to use not the end of a fiber but rather the illuminated partial region of a massive body as a measurement-sensitive surface) is in principle also suitable in the spatial high-resolution measurement of an ultrasonic field since the spatial resolution capability is determined solely by the size of the illuminated region, independent of the larger dimensions of the transparent body.

In an embodiment of the invention, the light strikes the illuminated area at an angle of incidence that is clearly smaller than the critical angle of total reflection and in particular is smaller than half the critical angle of total reflection. The sensitivity decreases relative to an arrangement with light incident close to the critical angle of total reflection, due to the incidence with an angle of incidence significantly deviating from the critical angle of total reflection; but it is advantageous that the measurement arrangement is insensitive to insignificant changes of the angle of incidence since the reflectivity for angles of incidence that are clearly smaller than the critical angle of total reflection is nearly independent of the angle of incident. Moreover, given such an angle of incidence and in particular in the region of perpendicular incidence (angle of incidence 0°), the reflectivity changes nearly linearly with the index of refraction of the fluid medium (and thus also with the acoustic pressure), such that the reflected intensity is likewise approximately linear relative to the acoustic pressure.

The boundary surface of the body is in particular planar and the illuminated area is clearly smaller than the boundary surface. In other words: the boundary surface is multiple times larger than the illuminated area. In an embodiment, the body can then be arranged such that it can be spatially varied relative to the path of the light propagating in it towards the boundary surface, such that the illuminated area can be positioned at different points of the boundary surface depending on the position of the body. In the case of a possible damage to the boundary surface in the illuminated area this can be relocated to another location. Given a cuboid-shaped body, this occurs by displacement parallel to the boundary surface. The body can also exhibit the shape of a polygon with planar flat sides situated opposite one another. In this case, a variation of the position of the illuminated area can ensue at a boundary surface of the body via rotation of the body around an axis of symmetry parallel to these flat sides.

The optically-transparent body preferably has a refractive index that lies optimally close to the refractive index of the fluid medium. The static reflectivity (i.e. the reflectivity in the presence of an ultrasound field) is then minimal and the signal-to-noise ratio is maximal.

In a further embodiment of the invention, the illuminated area is at least approximately shaped like a circular disc. In this manner it is ensured that the sensitivity of the hydrophone is independent of its rotary position relative to the propagation direction of the light.

DESCRIPTION OF THE PREFERRED EMBODIMENTS

Figure 1:
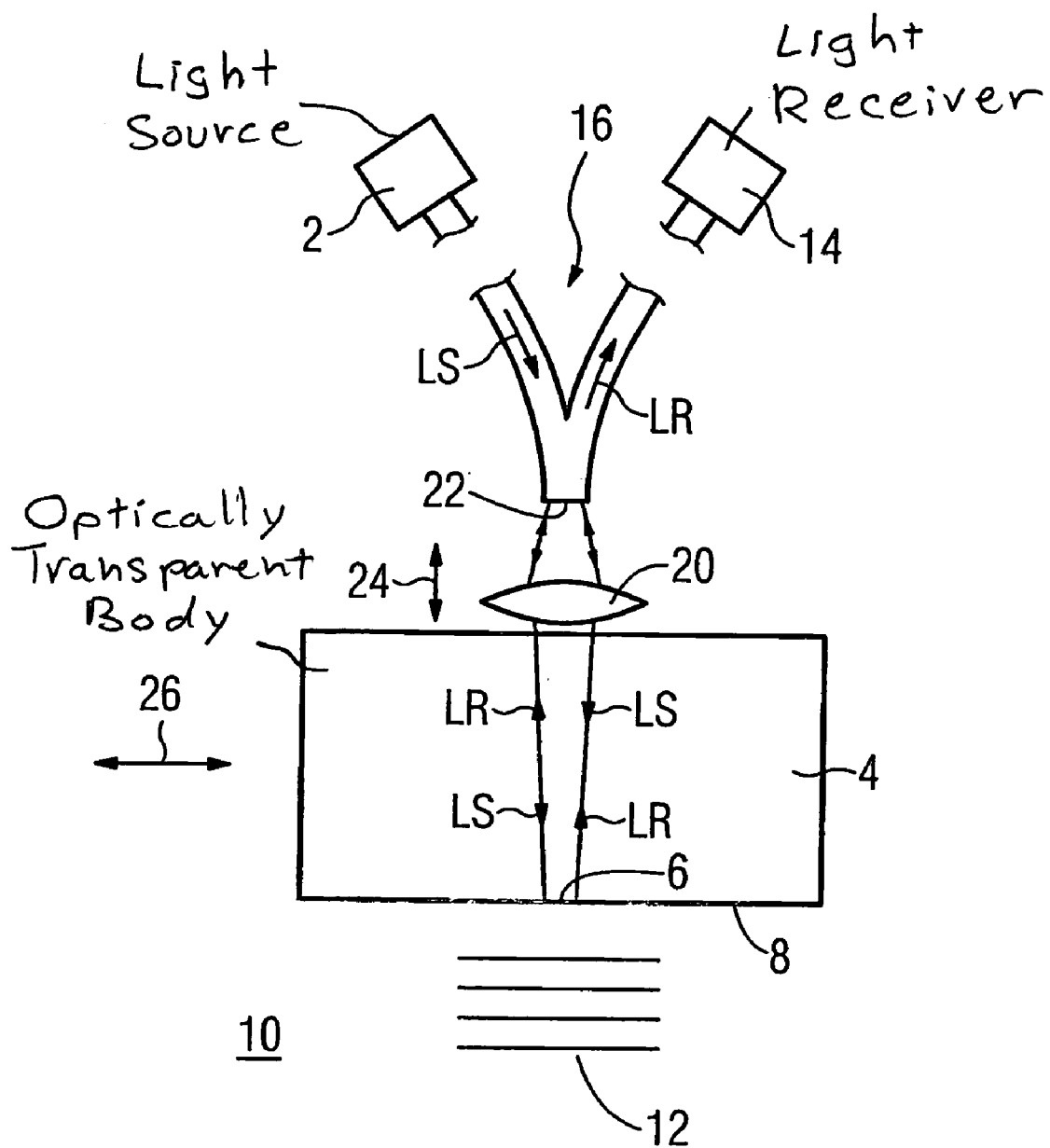
FIG. 1 is a schematic illustration of a first embodiment of an optical hydrophone constructed and operating according to the present invention.

According to FIG. 1, an optical hydrophone has a light source 2 for generation of light LS (in the exemplary embodiment a laser diode) that is injected into a transparent body 4, in the example an approximately cubic block comprised of glass (in the exemplary embodiment quartz glass with an index of refraction $n_K$=1.45 given a wavelength of 800 nm). Both the thickness and the lateral dimensions of the body 4 lie in the range of 1 mm to 50 mm. The transmitted light LS propagates freely within the body 4, i.e. without reflection on the walls of the body 4, and illuminates at least approximately laterally (i.e. given a body 4 made from glass with an opening angle smaller than 10° (the opening angle is shown enlarged in FIG. 1)) a circular disc-shaped areal region 6 of a planar boundary surface 8. A part of the light LS striking the area 6 is reflected there. Given a perpendicular incidence, the intensity of the reflected light LR depends only on the intensity of the incident light LS and the refraction index $n_K$ of the body 4 and $n_M$ of the fluid medium 10 (in the present case water with a refraction index $n_M$=1.34 at 800 nm) located outside of the body 4.

An ultrasound wave 12 incident on the boundary surface 8 generates a modulation of the refraction index $n_M$ of the fluid medium 10 (the modulation of the refraction index $n_K$ of the body 4 that is generated by the ultrasound wave is negligible) and thus a modulation of the intensity of the light LR reflected on the boundary surface 8. The time curve of the intensity of the reflected light LR is measured in a light receiver 14 (for example a photodiode) and is a direct measure for the time curve of the acoustic pressure in the illuminated areal region 6.

In the exemplary embodiment, the transmitted light LS and the reflected light LR outside of the body 4 are conducted in a light conductor arrangement 16, with a y-coupler is provided for sectioning of the light paths.

However, in principle it is also possible for the light 2 to freely propagate between the light source 2 and the body 4 or between the body 4 and the light receiver 14. Beam splitters can then be used for decoupling of the two light paths.

For focusing the emitted light LS onto the boundary surface 8, imaging optics 20 are provided that represents the exit aperture 22 of the y-coupler 18 (that, at the same time, is the entrance aperture 22 for the reflected light LR) on the boundary surface 8. In the exemplary embodiment, the exit aperture 22 is 0.125 mm and can be enlarged via displacement of the imaging optic 20 (arrow 24) 1 mm.

The imaging optic 20, the y-coupler 18 or the beam splitter can also be arranged inside the body 4 such that a more compact and insensitive design of the hydrophone is possible.

The body 4 can be arranged such that it can be shifted relative to the imaging optics 20 transverse to its optical axis (transverse to the light path or transverse to the normal of the areal region 6 or of the boundary surface 8), as is illustrated by the arrow 26. If damage occurs to the surface of the body 4 in the area of the illuminated areal region 6 due to the ultrasound pulse or due to cavitation bubbles, the body 4 can be shifted by a few mm until the illuminated areal region 6 again comes to lie at an undamaged point of the body 4.

The necessity of the use of a beam splitter or a y-coupler is omitted when the light LS generated by the light source 2 impinges on the boundary surface 8 at an angle deviated from 0°. In this case, incident light LS and reflected light LR are dependent on the angle of incidence and decoupled from the beam diameter according to corresponding distances, i.e. exit aperture and entrance aperture can be arrange spatially separate from one another such that the fiber optic arrangement can be made up of separate optical fibers. Moreover, the imaging optics 20 can then also be spatially divided into an imaging optic for the emitted light LS and imaging optics for the reflected light LR.

Figure 2:
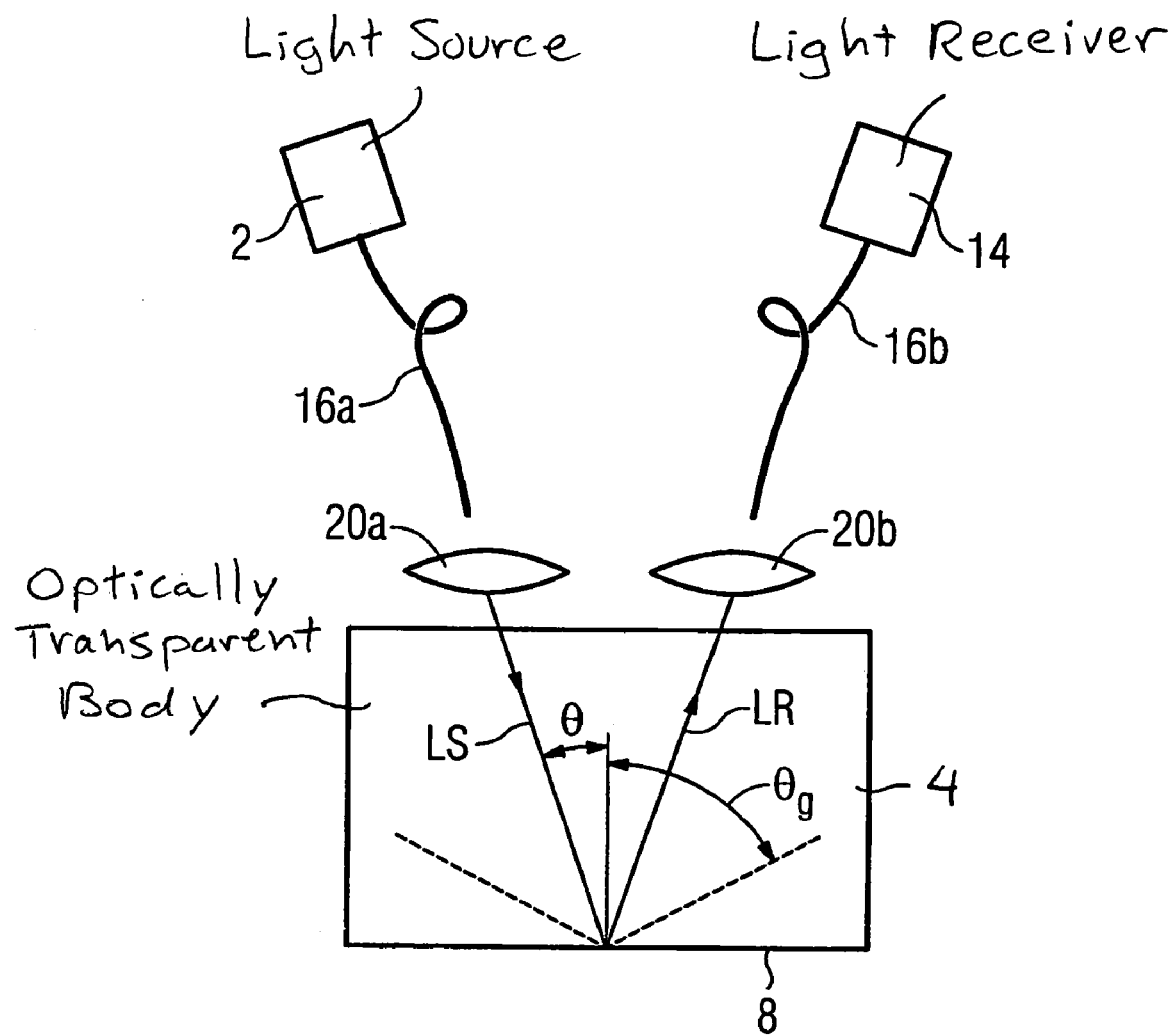
FIG. 2 is a schematic illustration of a second embodiment of an optical hydrophone constructed and operating according to the present invention.

FIG. 2 shows such an exemplary embodiment, according to which the light LS generated by the light source impinges at an angle of incidence θ deviating from 0°, however is clearly smaller than the critical angle $\theta_g$ of total reflection. An angle of incidence θ (at which the dependence of the reflectivity on the angle of incidence θ is only slight) is clearly smaller than the critical angle $\theta_g$ of total reflection in the sense of the invention. This is the case in practice for angles of incidence θ that are in particular smaller than $\theta_g/2$, preferably smaller than $\theta_g/3$. In the present case—given $n_K=1.45$ and $n_m=1.34$ and a critical angle $\theta_g$ of total reflection of 67°—these angles of incidence are θ<33° or θ<22°. In a practical embodiment, an angle of incidence of 10° has proven to be particularly suitable.

Due to the larger angle of incidence θ, the light paths of the generated light LS and of the reflected light LR outside of the body 4 are spatially separate from one another such that, to map on the boundary surface 8 the light LS exiting from the exit aperture of the light conductor 16a and to inject the reflected light LR into the entrance aperture (spatially separate from the exit aperture) of the light conductor 16b, imaging optics 20a or 20b that are likewise spatially separate from one another can be used.

Although modifications and changes may be suggested by those skilled in the art, it is the invention of the inventors to embody within the patent warranted heron all changes and modifications as reasonably and properly come within the scope of their contribution to the art.

We claim:

1. An optical hydrophone for measurement of an acoustic pressure distribution in a fluid medium, comprising:
   an optically transparent body having a boundary surface adapted to interface with said fluid medium, said optically transparent body having a cross-section and having an index of refraction that is substantially independent of acoustic pressure;
   a light source arrangement that emits light in a beam propagating freely through said optically transparent body and into said fluid medium, said beam having a cross-section that is smaller than said cross-section of said optically transparent body and said light source arrangement illuminating, with said beam, an area disposed at said boundary surface that is smaller than said boundary surface; and
   a light receiver arrangement for measuring an intensity of light reflected at said illuminated area as a measurement of said acoustic pressure distribution in said fluid medium, due to modification of the refractive index of said fluid medium caused by said acoustic pressure distribution.

2. An optical hydrophone as claimed in claim 1 wherein said light source arrangement illuminates said area with an angle of incidence that is smaller than half of a critical angle of total reflection in said optically transparent body.

3. An optical hydrophone as claimed in claim 2 comprising a fiber-optic arrangement having a first optical conductor that transmits light from said light source arrangement to said optically transparent body and a second optical conductor, separate from said first optical conductor, that transmits light from said optically transparent body to said light receiver arrangement.

4. An optical hydrophone as claimed in claim 3 comprising a first imaging element disposed between said first optical conductor and said optically transparent body and a second imaging element disposed between said optically transparent body and said second optical conductor.

5. An optical hydrophone as claimed in claim 2 wherein said light from said light source arrangement substantially laterally illuminates said area of said boundary surface.

6. An optical hydrophone as claimed in claim 5 wherein said light source arrangement illuminates a substantially circular disk as said area of said boundary surface.

7. An optical hydrophone as claimed in claim 1 comprising an optical fiber arrangement having a common conductor that conducts light from said light source arrangement to said optically transparent body and that conducts light from said optically transparent body to said light receiver arrangement.

8. An optical hydrophone as claimed in claim 7 wherein said optical fiber arrangement comprises an exit aperture from which light from said light source arrangement exits toward said optically transparent body, said exit aperture also serving as an entrance aperture for said reflected light.

9. An optical hydrophone as claimed in claim 8 wherein said optical fiber arrangement comprises a y-coupler.

10. An optical hydrophone as claimed in claim 8 comprising an imaging element disposed between said exit aperture and said optically transparent body.

11. An optical hydrophone as claimed in claim 10 wherein said imaging element forms an image of said exit aperture on said boundary surface as said area.

12. An optical hydrophone as claimed in claim 1 wherein said boundary surface is a surface of said optically transparent body.

13. An optical hydrophone as claimed in claim 1 wherein said optically transparent body is spatially variable relative to a path of said light propagating therein toward said boundary surface.

* * * * *